United States Patent
Hengge et al.

(10) Patent No.: US 6,943,267 B1
(45) Date of Patent: Sep. 13, 2005

(54) THIOPHOSPHONATE INHIBITORS OF PHOSPHATASE ENZYMES AND METALLOPHOSPHATASES

(75) Inventors: Alvan Carl Hengge, Smithfield, UT (US); Krzysztof Jerzy Swierczek, Logan, UT (US)

(73) Assignee: Utah State University, North Logan, UT (US)

( * ) Notice: Subject to any disclaimer, the term of this patent is extended or adjusted under 35 U.S.C. 154(b) by 120 days.

(21) Appl. No.: 10/346,672

(22) Filed: Jan. 16, 2003

Related U.S. Application Data

(63) Continuation-in-part of application No. 10/229,050, filed on Aug. 26, 2002.
(60) Provisional application No. 60/314,716, filed on Aug. 24, 2001.

(51) Int. Cl.$^7$ .............................. C07F 9/22; C07F 9/02; C07C 273/00
(52) U.S. Cl. ................................ 562/9; 558/9; 558/179
(58) Field of Search .............................. 562/9; 558/179, 558/8

(56) References Cited

U.S. PATENT DOCUMENTS

| | | | |
|---|---|---|---|
| 5,072,032 A | * 12/1991 | McKenna | 562/9 |
| 5,183,812 A | * 2/1993 | McKenna | 514/120 |
| 5,527,288 A | 6/1996 | Gross et al. | |
| 5,656,284 A | 8/1997 | Balkin | |
| 5,736,154 A | 4/1998 | Fuisz | |
| 5,788,980 A | 8/1998 | Nabahi | |
| 5,827,531 A | 10/1998 | Morrison et al. | |
| 5,830,506 A | 11/1998 | Taylor | |
| 5,848,991 A | 12/1998 | Gross et al. | |
| 5,874,098 A | 2/1999 | Stevens et al. | |
| 5,997,501 A | 12/1999 | Cross et al. | |
| 6,041,775 A | 3/2000 | Century | |
| 6,060,069 A | 5/2000 | Hill et al. | |
| 6,103,256 A | 8/2000 | Nabahi | |
| 6,143,716 A | 11/2000 | Meers et al. | |
| 6,238,284 B1 | 5/2001 | Dittgen et al. | |
| 6,251,418 B1 | 6/2001 | Ahern et al. | |
| 6,284,262 B1 | 9/2001 | Place | |
| 6,322,808 B1 | 11/2001 | Trautman et al. | |
| 6,339,069 B1 | 1/2002 | Meers et al. | |
| 6,348,210 B1 | 2/2002 | Gale | |
| 6,361,760 B1 | 3/2002 | Murata et al. | |
| 6,367,929 B1 | 4/2002 | Maiden et al. | |
| 6,372,248 B1 | 4/2002 | Qin et al. | |
| 6,372,813 B1 | 4/2002 | Johnson et al. | |
| 6,375,975 B1 | 4/2002 | Modi | |

OTHER PUBLICATIONS

Author: K.M. Holtz; B. Stec; J.K. Myers, S.M. Antonelli; T.S. Widlanski; E.R. Kantrowitz Title: Alternative modes of binding in two crystal structures of alkaline phosphatase–inhibitor complexes Protein Science (2000); 9:907–915; (Mar. 23, 2000).

Author: Frank Rusnak and Pamela Mertz; Title: Calcineurin: Form and Function; Physiological Reviews, vol. 80, No. 4, Oct. 2000; pp. 1483–1521.

Author: Philip Cohen; Title: Signal integration at the level of protein kinases, protein phosphatases and their substrates; TIBS 17—Oct. 1992; pp. 408–413.

Author: Philip Cohen; Title: The Croonian Lecture 1998. Identification of a protein kinase cascade of major importance in insulin signal transduction; The Royal Society, 1999; pp. 485–495.

Author: Mitchell J. Pulwer and Terry M. Balthazor; Title: A Convenient Synthesis of Aminomethylphosphonic Acid; Synthetic Communications, 16(7), 1986; pp. 733–739.

Author: Bruce P. Branchaud and Pei Tsai; Title: Relative Ease of Transient Acyl Imine Formation via Selenoxide, Sulfoxide, and Sulfone N–H Elimination. A Feasibility Study on the Preparation of Novel Peptide Analogues; American Chemical Society, 1987, 52, pp. 5475–5478.

Author: J.K. Myers, S.M. Antonelli, T.S. Widlanski; Title: Motifs for Metallophosphatase Inhibition; American Chemical Society; 1997; 119; pp.:3163–3164.

Author: Richard T. Lewis, W.B. Motherwell; Title: Some Novel Routes to 1–Hetero–Substituted 1–Vinylcyclopropanes; Department of Chemistry, Imperial College of Science, Technology and Medicine; vol. 48, pp. 1465–1466.

Author: Edwin M. Smolin, Lorence Rapoport; Title: s–Triazines and Derivatives; The Chemistry of Heterocyclic Compounds; 1959, pp.: 472–485.

Author: H.K. Kole; M.S. Smyth; P.L. Russ; T.R. Burke; Title: Phosphonate inhibitors of protein–tyrosine and serine/threonine phosphatases; Boi–Chem J. (1995) 311, pp. 1025–1031.

(Continued)

*Primary Examiner*—Kevin E. Weddington
(74) *Attorney, Agent, or Firm*—Meyer & Associates, LLC; Lee G. Meyer, Esq.

(57) ABSTRACT

Compounds of the general formula

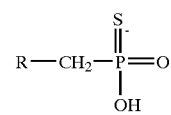

wherein R is selected from the group consisting essentially of hydrogen, methyl, ethyl, phenyl, a carboxyl, or naphthyl substituted or a carbonyl substituted, alkyl of from 3 to 20 carbon atoms, a mono, bi or tri cyclic aryl or substituted aryl for the inhibition of phosphatase enzymes, including metallophosphatases; and, novel methods for synthesizing such compounds. The methods of use include the administration of an effective amount of the compound to provide effective phosphatase inhibition and therapeutic use to treat or prevent certain diseases, which utilize specific phosphatase enzymes.

9 Claims, 2 Drawing Sheets

OTHER PUBLICATIONS

Author: Meng Taing; Yen–Fang Keng; Kui Shen; Li Wu; David S. Lawrence; Zhong–Yin Zhang; Title: Potent and Highly Selective Inhibitors of the Protein Tyrosine Phosphatase 1B; Biochemistry, 1999, pp. 3793–3803.

Author: Omar A. Ibrahimi; Li Wu; Kang Zhao Zhong–Yin Zhang; Title: Synthesis and Characterization of a Novel Class of Protein Tyrosine Phosphatase Inhibitors; Bioorganic and Medicinal Chemistry Letters, 10; 2000, pp. 457–460.

Author: Sir John Cornforth; John R.H. Wilson; Title: A General Reagent for O–Phosphonomethylation of Phenois; School of Chemistry and Molecular Sciences; University of Sussex; J. Chem. Soc. Perkin Trans. 1994; pp.: 1897–1900.

Author: T.R. Burke Jr.; Bin Ye; Xinjian Yan; Shaomeng Wang; Zongchao Jia; Li Chen, Zhong–Yin Zhang, David Barford; Title: Small Molecule Interactions with Protein—Tyrosine Phosphatase PTP1B and Their Use in Inhibitor Design; Biochemistry, 1996, pp.: 15989–15996.

Author: Spande, Thomas; Title: Synthesis of Two Novel Phosporylcholine Esters for Probes in Immunological Studies; J. Org. Chem, 1980, 45, 3081–3084.

Quin, L.D. (2000) "The acids of organophosphorus chemistry and their derivatives", in: A Guide to Organophosphorus Chemistry, pp. 155–156 John Wiley & Sons, New York.

Author: M. Aladzheva, I.L. Odinets et al.; Title: Phase–Transfer Catalytic Alkylation of Hydrothiophosphoryl Compounds; Russian Journal of General Chemistry; vol. 63, No. 3, Part 2, 1993, pp.: 431–437.

Author: B. Borecka, J. Chojnowski, et al.; Title: Synthetic and Mechinistic Aspects of the Reaction of Trialkylsilyl Halides with Thio and Seleno Esters of Phosphorus, Journal of Organometallic Chemistry, 171 (1979), 17–34.

Author: N.N. Mel'nikov, B.A. Khashin, et al.; Title: Thione–Thiol Isomerization of Some Phosphorothioic and Phosphorodithioic Esters in Their Reaction with Amines; Organic Insectofungicides, 1963, pp. 2394–2398.

Author: H.Z. Lechner, R.A. Greenwood et al.; Title: The Phosphonation of Aromatic Compounds with Phosphorus Pentasulfide; Contribution from the Research Division, American Cyanamid Co. (Jan. 24, 1956), vol. 78, pp. 5018–5022.

Author: Tsutomu Yokomatsu, Hiroaki Takechi, et al.; Title: Aryldifluoromethylphosphonothioic Acids from O,O–Diethyk Aryldifluoromethylphosphonothioates; J. Org. Chem 2000, 65; pp.: 5858–5861.

Author: C.E. McKennam T.G. Ye, et al.; Title: Design and Synthesis of Organophosphorus Compounds with Antiviral and other Bioactivities; Phosphorus, Sulfur, and Silicon, 1990, vol. 49/50; pp.: 183–186.

Author: Charles E. McKenna, Zeng0Min Li, et al.; Title: Simple and Conjugate Bifunctional Thiophosphonates, Synthesis and Potential as Anti–viral Agents; Phosphorus, Sulfur, and Silicon, 1993, vol. 74, pp. 469–470.

Author: Serge R. Piettre, Pierre Roboisson; Title: Easy and General Access to α,α–Difluoromethylene Phosphonothioic Acids. A New Class of Compounds; Tetrahedron Letters, vol. 37, No. 13, pp. 2229–2232.

Author: Nguyen Thanh Thuong, Jean–Pierre Chabrier; Title: No. 134—Contribution a L'etuden de L'isomerisation des sels des Acides Thophosphoriques et Thiophosphoniques, Bulletin De La Societe De France, 1970, No. 2, pp. 780–787.

Author: Von Gunter Hilgetag, Herbert Teichmann; Title: Uber einige Methylierungsreaktionen der Beiden Isomeren Trimethylthiophosphate; Beitrage zur Chemie der Thiophosphate. II, 1958, pp. 90–96.

N.G. Zabirov, R.A. Cherkasov, et al.; Title: Method for the Preparation of Acid Phosphorothioites and Phosphonothioates; UDC 547.26'118, 1986, pp. 1047–1048.

Author: Kabachnik, Mastryukova et al; Title: Reactivity of alkali salts of acid esters of alkylthiophosphonic acids; Chemical Abstracts, Vo. 51, 1957, p. 1823.

Author: Bakanova, et al.; Title: Reaction of dialkyl chlorothiophosphates with nitrophenol in the presence of pyridine hydrochloride; Chemical Abstracts, Vo. 51, 1957, pp. 1823–1824.

* cited by examiner

| Inhibitor | Human AP | E. Coli AP | YOP | pp2c | λ AP |
|---|---|---|---|---|---|
| Me—P(=S)(—OH)(O⁻) C₆H₁₁NH₃⁺ | 15.8 mM | no inhibition | 10.4 mM | 2.3 mM | ~20 mM |
| Pr—P(=S)(—OH)(O⁻) HNMe₃⁺ | 0.72 mM | no inhibition | no inhibition | 0.36 mM | 8.8 mM |
| Bn—P(=S)(—OH)(O⁻) HNMe₃⁺  (Bn = CH₂Phenyl) | 0.21 mM | no inhibition | no inhibition | 0.26 mM | 0.7 mM |
| MeO-CO-(CH₂)₅-P(=S)(—OH)(O⁻) PhNH₃⁺ | 0.6 mM | no inhibition | no inhibition | 0.24 mM | 1.1 mM |
| HO-CO-(CH₂)₅-P(=S)(—OH)(O⁻) C₆H₁₁NH₃⁺ | 1.76 mM | no inhibition | >50 mM | 0.27 mM | 0.91 mM |
| 8-COOH-naphthyl-CH₂-P(=S)(—OH)(O⁻) HNMe₃⁺ | 2.8 mM | no inhibition | 0.22 mM | 14 μM (!) | 93 μM |

Figure 2

THIOPHOSPHONATE INHIBITORS OF PHOSPHATASE ENZYMES AND METALLOPHOSPHATASES

CROSS-REFERENCE TO RELATED APPLICATION

This application is a continuation-in-part of U.S. application Ser. No. 10/229,050 for INHIBITORS OF PHOSPHATASE ENZYMES AND METALLOPHOSPHATASES filed Aug. 26, 2002, which in turn claims benefit of U.S. Provisional Application No. 60/314,716, filed Aug. 24, 2001.

STATEMENT REGARDING FEDERALLY SPONSORED RESEARCH

The U.S. Government funded portions of the research leading to this invention.

BACKGROUND OF THE INVENTION

1. Field of the Invention

The previous invention related generally to compounds effective as inhibitors of phosphatase enzymes and metallophosphatases, and specifically to chemical compounds that are inhibitors of phosphatase enzymes, their method of manufacture; and, particularly use of a class of chemical compounds as inhibitors of phosphatase enzymes including metallophosphatases. The present invention relates to thiophosphonates as inhibitors of phosphatases and particularly metallophosphatases, and a method of preparation of these thiophosphonate inhibitors.

2. Description of Related Art

Phosphate esters are ubiquitous in living organisms. Recently, the key role of the phosphorylation and dephosphorylation of proteins in the control of a host of biochemical processes within living organisms, and especially hunans, have been appreciated. The chemistry of phosphate esters makes them particularly suited for the basis of a regulatory mechanism and therefore provides a potential tool for biological analysis and treatment.

While the hydrolysis of a phosphate monoester, such as serine phosphate or methyl phosphate, is thermodynamically favorable, the activation barrier is formidable. Under physiological conditions (neutral pH, 25° C.) methyl phosphate has an estimated half-life for unanalyzed hydrolysis of about 500,000 years. The relative inertness of phosphate esters in the absence of enzymatic catalysis makes them a logical bases for a control mechanism and therefore as possible mechanism in the treatment of certain types of disease or conditions.

Protein kinases and phosphatases are now known to be the key cellular players in the process of signaling and the balance between phosphorylation and dephosphorylation of proteins. They have been shown to regulate a wide range of biochemical processes, including metabolism, DNA transcription and replication, cell differentiation, and immune responses.

Protein targets are phosphorylated at specific sites by one or more protein kinases, and the reverse reactions (hydrolysis of the phosphate esters) are catalyzed by protein phosphatases. Despite the fact that this phosphorylation/dephosphorylation process often takes place far from active sites, these processes function as a control between active and inactive states for many enzymes. The activation effects can be dramatic, often resulting in rate accelerations of $10^2$ to $10^5$-fold. The critical role played in regulating metabolism by phosphorylation and the counterbalancing roles played by kinases and phosphatases is well established (see Cohen, P. "Signal integration at the level of protein kinases, protein phosphatases and their substrates" *Trends Biochem Sci* 17, (1992) 408–13. and Cohen, P. "The Croonian Lecture 1998.; Identification of a protein kinase cascade of major importance in insulin signal transduction" *Philos Trans R Soc Lond B Biol Sci* 354, (1999) 485–95.)

In addition, the reversible phosphorylation of proteins is the chemical basis of a major mechanism of signal transduction in both prokaryotes and eukaryotes. These signaling pathways are used for transmitting signals across the cytoplasm to the nucleus, to induce the transcription of particular genes via the phosphorylation and activation of transcription factors. The signal cascade is activated following the binding of ligands, such as growth factors and cytokines to cell surface receptors, or in response to cellular stresses.

Thus, phosphatase enzymes are critical in the catalysis of the transfer of a phosphoryl group from a phosphomonoester or a phosphoanhydride to water, producing inorganic phosphate. The Ser/Thr phosphatases possess binuclear metal centers (metallophosphates) and transfer the phosphoryl group directly to a metal-coordinated hydroxide molecule. These enzymes dephosphorylate both phosphoserine and phosphothreonine amino acids in proteins. The protein-tyrosine phosphatases (PTPases) do not contain metal ions but use a cysteine nucleophile to form a phosphorylated cysteine intermediate.

Metallophosphatases, as indicated above, are a subfamily of phosphatases and include all of the alkaline phosphatases, and all members of the Serine/Threonine family of protein phosphatases (calcineurin, lambda, and PP2C as used herein). These enzymes and a number of others have been structurally characterized by X-ray crystallography. They are shown to have two metal ions at the active site that is used in catalysis. In metallophosphatases distances that vary in a narrow range separate the metal ions. The identities of the metal ions vary. Alkaline phosphatases contain two zinc ions. Calcineurin contains a ferric ion (Fe in the +3 state) and a zinc ion (zinc +2). The physiological metal ions utilized by other metallophosphatases are uncertain. The enzymes function with a variety of divalent metal ions, and most typically they are studied using manganese ions ($Mn^{+2}$) or, less commonly, magnesium.

Phosphatases are, therefore, essential enzymes in the regulation of many biochemical pathways in living organisms. They have been identified as essential virulence factors in a number of pathogenic bacteria that are crucial in the development of diabetes as well as the rejection of transplanted organs. Consequently, phosphatase enzyme inhibitors have useful applications as biochemical research tools in the study of the roles of these enzymes. As pharmaceuticals phosphatase enzyme inhibitors have potential use in the treatment of a wide variety of diseases, such as diabetes, autoimmune diseases, cancer, and viral infection, such as HIV.

The specific roles of only a few of the many known phosphatases are clearly understood. PP2B, also known as calcineurin, has an essential role in the production of T cells in the immune response pathway. (Rusnak, F. and Mertz, P. "Calcineurin: form and function" *Physiol Rev* 80, (2000) 1483–521.) Calcineurin is the target of the immunosuppressive drugs FK506 and cyclosporin A. The protein-tyrosine phosphatase PP-1B regulates the production of insulin, and is currently a major target of studies aimed at developing a selective inhibitor that might prove a viable treatment for diabetes. However the physiological roles of only a very small percentage of the many known phosphatases are understood.

A major hindrance to studies that would aid in this understanding has been the lack of selective inhibitors. In cellular or animal studies selectively inhibiting the enzyme and observing the biochemical results can be used to study the role of an enzyme in a biochemical pathway. There are several phosphatase inhibitor "cocktails" that are commercially available for this purpose, which contain a mixture of compounds that typically give only very broad specificity. For instance, two are available from Sigma-Aldrich, one of which will inhibit all protein-tyrosine phosphatase as well as alkaline phosphatases; the other inhibits all serine/threonine phosphatases plus alkaline phosphatases.

Human placental alkaline phosphatase (PLAP) is one of three tissue-specific human alkaline phosphatases extensively studied because of its expression in tumors and it is a well-known tumor marker.

This lack of selective inhibitors of phosphatases, and more importantly, specific subfamilies of phosphatases impedes biochemical studies aimed at determining the biological roles of specific phosphatases, as well as the development of effective treatment regimes and pharmaceuticals.

Many avenues have been pursued to create specific, effective phosphatase enzyme inhibitors, but none to date have been overly successful. One such phosphatase inhibitor, that has been extensively pursued, is the phosphonates. The phosphonate group is similar to the phosphate group that is present in the natural substrates of phosphatases and some appear to exhibit slight inhibition of a few protein phosphatases (Kole et. Al., Biochem. Journal, 1995, 311, 1025–1031; Taing et al., Biochemistry, 1999, 38, 3793–3803; Burke et al., Biochemistry, 35, 15989–15996.) The synthesis of a number of phosphonic acid inhibitors and their inhibition constants for several phosphatase enzymes were reported by Myers, Antonelli and Widlanski (Journal of the American Cancer Society, 1997, 119, 3163–3164.)

Additionally, heteroaromatic phosphonates with a thio ether linkage have been prepared previously as inhibitors of the enzyme fructose 1,6-bisphosphatase. In these compounds the heteroaromatic moiety is intended to mimic the fructose portion of the natural substrate. Several aryloxymethylphosphonates were prepared previously and evaluated as inhibitors of protein tyrosine phosphatases, and were found to be weak inhibitors with Ki values in the millimolar range (Ibrahimi et al., Bioorg. Med. Chem. Lett., 2000, 10: 457–460). However, none of the phosphatase inhibitors produced to date have inhibited phosphatase enzymes to a significant level. This has been due to many factors. One important factor is that binding of the phosphatase inhibitor has not interfered with the active region of the phosphatase enzyme. (Kantrowitz et al., Protein Science, 2000, 9:907–915.) In addition, the bond that has occurred between the phosphatase inhibitors produced to date and the phosphatase enzymes has been very weak.

Thus, phosphatase inhibitors that are specific and demonstrate high degrees of phosphate inhibition are needed to further study phosphate enzyme chemistry, as well as to treat and/or retard a wide variety of health conditions and diseases. In particular, phosphatase inhibitors that are not hydrolyzed by the phosphatase enzyme and exhibit a high degree of interference with the active region of the enzyme are needed.

In particular compounds which function, as inhibitors of metallophosphatases are important to these studies as well as to treat and/or retard a wide variety of health conditions and diseases. In our prior application, a specific class of compounds was discovered that exhibited a high degree of interference with the active region of the phosphatase enzyme and particularly metallophosphatase enzymes. The enzyme did not hydrolyze these compounds, thus providing an effective phosphatase enzyme inhibitor. The effectiveness of these compounds was attributable in part to their molecular footprint, which mimics the transition state of the phosphate ester hydrolysis reaction.

The class of compounds of that application were generally ethers represented by the general formula R—X—R'—$PO_3^{-2}$ wherein X is selected from the group consisting of O, NR", or S where R" is H or an organic moiety of from about 1 to about 100 carbon atoms; R' is a non hydrolysable moiety providing a bond spacing between P and X of from about 2.5 to about 4.5, and preferably from about 3 to about 4 Å; and, R is, a moiety that does not interfere with the bond spacing between P and X.

Another group of compounds that have been the subject of a number of patents and publications as antiviral compounds are the thiophosphonates, or phosphonothioic acids and their salts (See for example, Borecka, B., Chojnowski, J., Cypryk, M. and Zielinska, J. "Synthetic and mechanistic aspects of the reaction of trialkylsilyl halides with thio and seleno esters of phosphorus" *J. Organometallic Chem.* 171, (1979) 17–34; Piettre, S. R. and Raboisson, P. "Easy and general access to α,α-difluoromethylene phosphonothioic acids (See, Aladzheva, I. M., Odinets, I. L., Petrovskii, P. V., Mastryukova, T. A. and Kabachnik, M. I. "Phase-transfer catalytic alkylation of hydrothiophosphoryl compounds. IV. Reactions with primary alkyl halides." *Russ. J. Gen. Chem.* 63, (1993) 431–437) A new class of compounds." *Tetrahedron Letters* 37, (1996) 2229–2232; Yokomatsu, T., Takechi, H., Murano, T. and Shibuya, S. "Synthesis of aryldifluoromethylphsophonothioic acids from O,O-diethyl aryldifluoromethylphosphonothioates" *J. Org. Chem.* 65, (2000) 5858–5861 and Ladzheva, I. M., Odinets, I. L., Petrovskii, P. V., Mastryukova, T. A. and Kabachnik, M. J. "Phase-transfer catalytic alkylation of hydrothiophosphoryl compounds. IV. Reactions with primary alkyl halides." *Russ. J. Gen. Chem.* 63, (1993) 431–437). There is also evidence that this class of compounds has been investigated as plant growth regulators and as inhibitors of a number of different enzymes as well as lubricants and polymers.

While it has been unexpectedly discovered that certain of these compounds are effective as inhibitors of phosphatases and specifically metallophosphatases in accordance with the instant invention, as set forth below, current methods of preparation have heretofore not yielded satisfactory compounds on an acceptable yield bases.

Thus, while many known methods are suitable for the production of small amounts of very specific compounds they often utilize reaction conditions that would preclude large-scale production and/or the synthesis of derivatives bearing a variety of functional groups that would be useful. For example, methyl and, to a lesser extent, ethyl esters have often been used as protecting groups during syntheses of phosphates and phosphonates. However, while typically dimethyl or diethyl groups of phosphonate esters can be removed by treatment with trimethylsilyliodide or trimethylsilylbromide, this method works sparingly and results in less than satisfactory yields of thio derivatives. (See, McKenna, C. E., Li, Z. -M., Ju, J. -Y., Pham, P. -T., Kilkuskie, R., Loo, T. L. and Straw, J. "Simple and conjugate bifunctional thiophosphonates: synthesis and potential as anti-viral agents" *Phosphorus, Sulfur and Silicon* 74, (1993) 469–470.)

In addition, deprotection of the dibenzyl esters of α, α-difluoromethylenephosphonothioic acids has traditionally been accomplished by the cumbersome process of utilizing sodium in liquid ammonia. (See, Kabachnik, I., Mastryukova, T. A., Kurochkin, N. I., Rodionova, N. P. and Popov, E. M. "Reactivity of akali salts of acid esters of alkylthiophosphonic acids. Reactions of acylation and alkylation." *Zhur. Obschei Khim.* 26, (1956) 2228–2233.) Recently another method was reported that utilized a thionothiolo rearrangement followed by Pd-catalyzed deallylation in order to accomplish deprotection of diethyl α,α-difluoromethylenephosphonothioic (Zabirov, N. G., Cherkasov, R. A. and Pudovik, A. N. "Lawesson's reagent in the synthesis of organophosphorus compounds. I. Preparation of dialkyl thiophosphites and alkyl thiophosphonites." *Russ. J. Gen. Chem.* 56, (1986) 1047–1048.) Neither of these methods, however, has been found satisfactory for the production of large quantities of thiophosphonates.

All of these reported methodologies are time consuming, use very specific ester protecting groups, and are not applicable to large-scale production of phosphonothioic acids and/or the production of phosphonothioic acids with a wide range of functional groups. These prior methods for producing thiophosphonates, or phosphonothioic acids have shortcomings. First, the prior syntheses do not use methyl protecting groups, but instead use various other protecting groups that are particularly suited to the specific compound being synthesized, and which require methods for their removal that preclude general use. For example, one prior method uses benzyl ester protection, and removal using sodium in liquid ammonia. These are strong reductive conditions that would result in unwanted alterations in many functional groups if they were present in the compound.

Although, generally methyl-protecting groups are the standard in phosphate ester synthesis because they are easy to remove, using the prior art methods of thio derivative synthesis, the methyl groups are difficult to remove. Specifically, in the prior art synthesis removal of the first methyl group is relatively easy, but the second is recalcitrant. Further, the prior published synthesis can only be used for un reactive alkyl substituents. Additionally, the prior art methods require complex purification steps, which are cumbersome, and reduce yields.

It would therefore be advantageous to have a synthetic approach for producing thiophosphonates, or phosphonothioic acids by a facile method that involves only minimal purification procedures, and which is much more general than previous synthetic approaches. It would also be advantageous to have a synthetic approach for producing thiophosphonates, or phosphonothioic acids applicable to the preparation of a wide variety of these compounds bearing a variety of reactive functional groups, while requiring only a minimal purification of intermediates, and a final product purification and recovery by a simple crystallization of the pure form of the product compound.

Citation of the above documents is only a discussion of related art and not intended as an admission that any of the foregoing is pertinent prior art. All statements as to the date or representation as to the contents of these documents is based on subjective characterization of information available to the Applicants, and does not constitute any admission as to the accuracy of the dates or contents of these documents.

SUMMARY OF THE INVENTION

It has now been discovered that a class of compounds, some of which are previously known compositions, function, unexpectedly, as inhibitors of phosphatase enzymes and specifically metallophosphatases. These compounds structurally resemble the substrates of the enzymes, but bear the nonhydrolyzable thiophosphonate group in place of the phosphate ester moiety present in natural substrates, which makes these compounds ideal as inhibitors. Apparently, the presence of the sulfur atom enhances the affinity of these compounds for the binuclear center of metallophosphatases, making them particularly effective as metallophosphatase inhibitors.

Further, a new synthetic approach for producing members of this family of compounds has been developed that allows for synthesis by facile methods that involve increased yields, minimal purification procedures, and provides a method that is more general than previous synthetic procedures allowing the attachment of reactive R groups to the molecule. The novel synthetic approach of the instant invention represents a significant improvement over previous methods in that it does not require any chromatography or distillations.

It has now been discovered that a specific class of compounds of thiophosphonates of the following general formula:

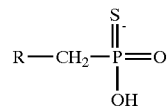

wherein R is selected from the group consisting essentially of hydrogen, methyl, ethyl, phenyl, a carboxyl, or naphthyl or a carbonyl substituted, alkyl of from 3 to 20 carbon atoms, a mono cyclic, bicyclic or polycyclic aryl or substituted aryl, exhibit a high degree of interference with the active region of the phosphatase enzyme and particularly metallophosphatase enzymes and are not hydrolyzed by the enzyme to provide an effective phosphatase enzyme inhibitor. Useful compounds are formed wherein R is selected from imidazole, indole, pyrrole, morpholine, isoxazole, pyrazole, amino acid, or a polypeptide.

The novel compounds of the present invention have formula:

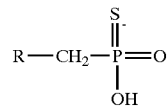

wherein R is selected from an carbonyl substituted alkyl of from about 3 to about 20 carbon atoms; or a mono, di, or tricyclic carbonyl substituted aryl and specifically an imidazole, indole, pyrrole, morpholine, isoxazole, pyrazole, amino acid, or a polypeptide and more specifically compounds of trimethylammonium salt of propylphosphonothioic acid; the trimethylammonium salt of benzylphosphonothioic acid; the anilinium salt of 6-thiophosphonohexanoic acid methyl ester, the p-methylanilinium salt of 6-thiophosphonohexanoid acid; and, p-methylanilinium salt of 7-thiophosphonomethylnaphthalene-1-carboxylic acid.

In accordance with the invention, effective inhibition of phosphatase enzymes is accomplished by contacting the phosphatase enzyme to be inhibited with an effective amount of a class of compounds represented by the general formula above, the exact form to be determined by the pH of the environment. In accordance with the invention, the above compounds are prepared in a synthesis wherein a methyl group is first removed from a single oxygen and reattached to the sulfur allowing both to be easily removed using a standard reagent often used for demethylation of esters (trimethylsilyl iodide). Unexpectedly, this methodology allows synthesis of more general compounds having a wider range of substituted moieties. In addition the only purification step in accordance with the instant invention is washing and recrystallizing the final product.

In accordance with the synthesis dimethyl thiophosphite is prepared from dimethyl

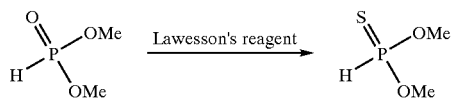

phosphite using Lawson's Reagent.

Then the dimethyl thiophosphite is deprotonated with a base and a phase transfer catalyst in accordance with the Michaelis-Becker alkylation to be used as a nucleophile with an alkyl halide as follows:

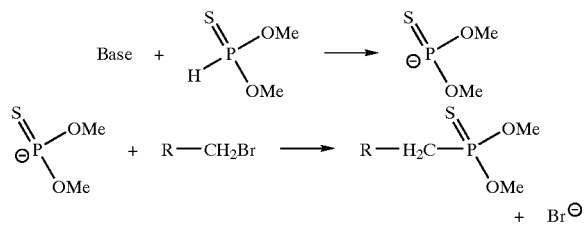

The resultant product is reacted with $Me_3N$ and then methyliodide to apparently, without limitation, transfer one oxygen methyl to the sulfur, resulting in

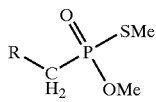

Which then can be treated with $SiI\ Me_3$ in a standard manner, to produce

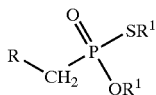

wherein $R^1$ is $Si\ Me_3$

Which when hydrolyzed and then contacted with a base yields the compound:

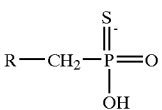

BRIEF DESCRIPTION OF THE DRAWINGS

The following drawings form part of the present specification and are included to further demonstrate certain embodiments. These embodiments may be better understood by reference to one or more of these drawings in combination with the detailed description of specific embodiments presented herein.

FIG. 2: Illustrates inhibition constants (Ki) of four phosphatase inhibitors of the general formula

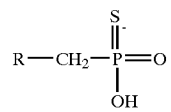

Figure 1:
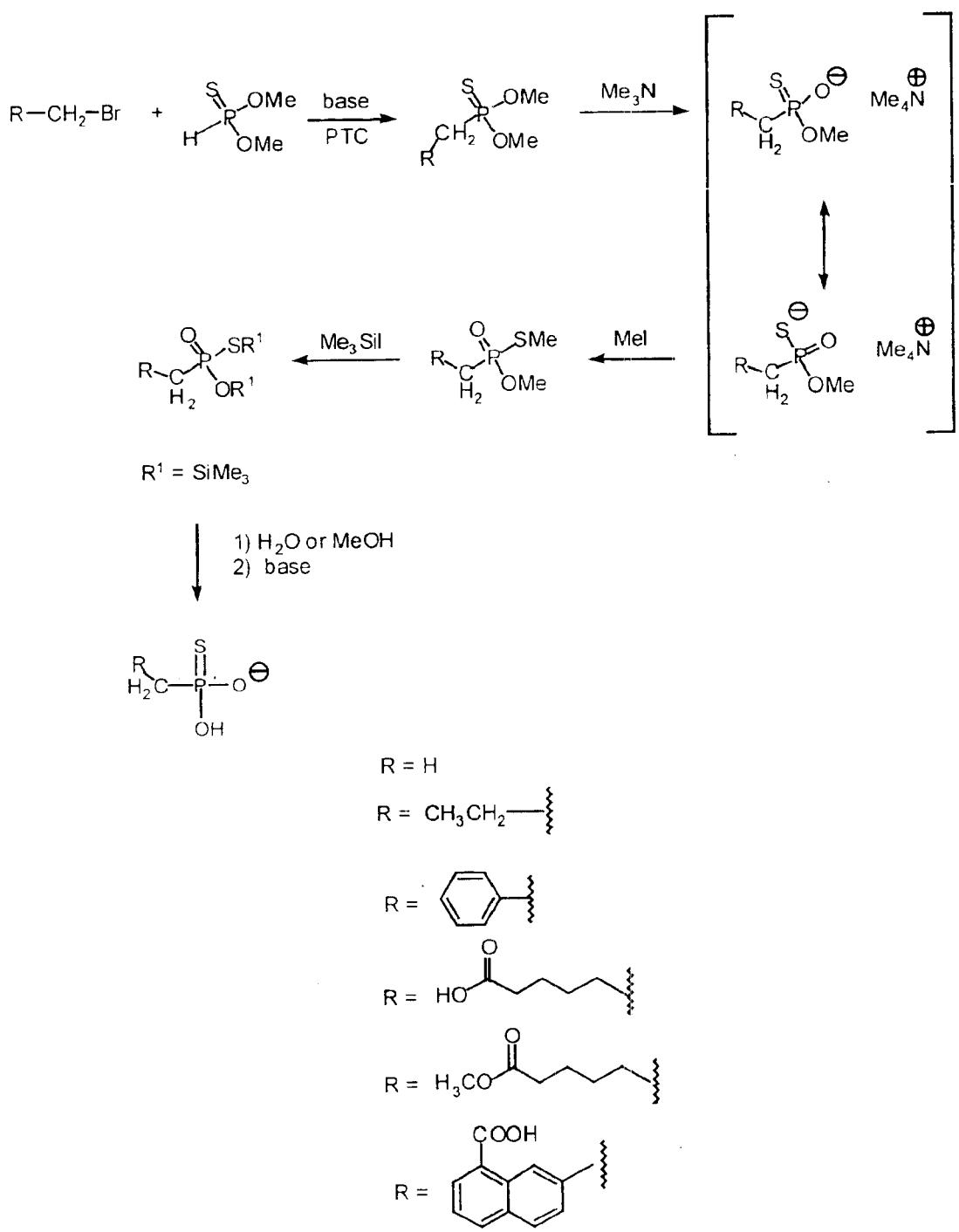
FIG. 1: Illustrates a general synthetic scheme for the synthesis of thiophosphonate salt compounds of the present invention.

wherein R equals propyl, benzyl, methyl and ethyl versus human alkaline phosphatase, *E. coli* alkaline phosphatase, *Yersinia* protein tyrosine phosphatase and the serine/threonine protein phosphatase 2C (PP2C) in accordance with methods of the present invention.

DESCRIPTION OF ILLUSTRIOUS EMBODIMENTS

Definitions:

For the purposes of the present invention, the following terms shall have the following meanings:

The term "PP2C" as used herein means a compound that is a member of the PPM family of serine-theonine phosphatases entitled, serine-threonine protein phosphatase 2C. It is a $Mn^{2+}$ or $Mg^{2+}$ dependent serine-threonine phosphatase involved in regulating cellular stress responses in eukaryotes by down-regulating mitogen-activated protein kinase pathways.

As used herein, "pharmaceutically acceptable salt" refers to those salts which retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-tolucnesulfonic acid, salicylic acid and the like.

As used herein, "thiophosphonates" and "phosphonothioic acids" refers to closely related molecules that are interchangeable by well-known methods in the art. These words can be used interchangeably and one skilled in the art will understand the meaning of each form (acid, salt or base) of the molecule.

Moreover, for the purposes of the present invention, the term "a" or "an" entity refers to one or more of that entity; for example, "thiophosphonate" or "a thiophosphonate" refers to one or more of those compounds or at least one compound. As such, the terms "a" or "an", "one or more" and "at least one" can be used interchangeably herein. It is also to be noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated or biologically pure compound is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

Synthetic Method:

Compounds of the present invention were produced according to the synthetic scheme in FIG. 1. This general synthetic scheme allows for the production of thiophosphonates bearing a wide variety of R-groups while utilizing simple, inexpensive reaction conditions and reagents. Such a method allows for commonly used protecting groups, such as methyl ester, which are easily available, inexpensive, and capable of producing many different types of thiophosphonates. Additionally, the method of the present invention does not require purification of intermediates or the final product. There are only minimal or elementary purification steps associated with this synthetic scheme. The final product merely needs to be crystallized and washed to be in a useable form. The advantages of this novel method results in relative high yields of thiophosphonates for a relatively low production cost due to all of these factors.

The synthetic methods of the present invention involve initially exchanging a sulfur atom for the double-bonded oxygen of dimethyl phosphite, using Lawesson's reagent in an organic solvent such as benzene and at reflux temperatures. Lawesson's reagent is an effective reagent to convert oxygen to sulfur in carbonyl groups such as those found in ketones or in converting phosphates to thiophosphites. The novel advantage of performing this step at the beginning of the synthetic scheme allows for the production of a wide variety of phosphonothioic acids bearing a range of functional groups. Functional groups susceptible to Lawesson's reagent are protected from later exposure by performing this oxo-thio conversion early in the synthetic scheme.

The exchange of a sulfur atom for the double-bonded oxygen of dimethyl phosphite is followed by the Michaelis-Becker alkylation to deprotonate the thiophosphite with a base. The deprotonated thiophosphite is used as a nucleophile with an alkyl halide. This reaction forms a bond between the phosphorus atom and the carbon of the alkyl halide to yield a substituted thiophosphite (See, FIG. 1) The addition of an alkyl halide R—CH$_2$—X to the thiophosphite ester in the presence of a base results in the production of the substituted O,O-dimethyl ester of the formula R—CH$_2$—P(S)(OCH$_3$)$_2$.

The alkyl halides useful in accordance with this invention generally have the formula R—CH$_2$—X, wherein X is a halide and preferably a bromide. As a group, alkyl halides are one of the most commonly available and inexpensive families of compounds that are commercially available.

Examples of alkyl halides are 1-iodopropane; benzyl chloride (or bromide or iodide); 6-bromohexanoic acid tert-butyl ester; 7-bromomethylnaphthalene-1-carboxylic acid tertbutyl ester; methyl bromide (or iodide or chloride); ethyl bromide (or iodide or chloride); iodoacetic acid; 1-bromobutane; 2-bromobutane; 1-bromopentane; etc.

In a particular embodiment, the thiophosphite ester is O,O-dimethylphosphonothioate. Other examples of useful O,O-dimethyl esters include O,O-dimethylpropylphosphonothioate, O,O-dimethylbenzylphosphonothioate, 6-(dimethoxythiophosphoryl)hexanoid acid tert-butyl ester and 7-(dimethoxythiophosphorylmethyl)naphthalene-1-carboxylic acid tert-butyl ester.

Bases useful for the Michaelis-Becker alkylation are for example sodium hydroxide and anhydrous potassium carbonate, however it is possible to use any strong base A two-step rearrangement of O,O-dimethylphosphonothioate then is accomplished in accordance with the invention. First a mono-deprotection with trimethylamine under mild conditions reduces O,O-dimethylphosphonothioate (See, FIG. 1). Reduction of the O,O-dimethyl ester is then followed by reaction with methyl iodide to produce the corresponding O,S-dimethyl ester (See, FIG. 1) which, in contrast to an O,O-dimethyl ester, readily undergoes deprotection by trimethylsilyl iodide to produce an disilyl ester (See, FIG. 1) This in turn is easily and rapidly hydrolyzed according to the present invention to give the final thiophosphonate product.

Traditionally, dimethyl esters have been difficult to deprotect, as have dialkyl esters of phosphonothioic acids.

(See, McKenna, C. E., Li, Z. -M., Ju, J. -Y., Pham, P. -T., Kilkuskie, R., Loo, T. L. and Straw, J. "Simple and conjugate bifunctional thiophosphonates: synthesis and potential as anti-viral agents" Phosphorus, Sulfur and Silicon 74, (1993) 469–470.) In the synthetic scheme of the present invention, by removing a methyl group from one of the oxygen atoms, and replacing this methyl group on the sulfur atom, the methyl moieties are readily removed leaving the rest of the molecule in tact. For example, propylphosphonothioic acid O, O-dimethyl ester (See FIG. 1) does not react with iodotrimethylsilane at room temperature or in boiling dichloromethane, and in refluxing tetrachloromethane decomposition results.

Thus, the first step of the above-mentioned process is to effect the removal of a first methyl group by treatment with trimethylamine in acetone or n-butyl amine in benzene to convert the O,O-dimethylphosphonothioate into its O-methylphosphonothioic acid, tetramethylammonium salt. In certain embodiments, the O-methylphosphonothioic acid, tetramethylammonium salt is selected from O-methylbenzylphosphonothioic acid, tetramethylammonium salt; methylbenzylphosphonothioic acid, tetramethylanmmonium salt; 6 (hydroxymethoxythiophosphoryl) hexanoic acid tert-butyl ester, tetramethylammonium salt; and 6-(hydroxymethoxythiophosphoryl)hexanoic acid tert-butyl ester.

The monomethylated compound (See, FIG. 1) is then dissolved in dichloromethane and reacted with methyl iodide to produce an O,S-dimethyl ester (See, FIG. 1.) After reaction with methyl iodide, the reaction mixture is refluxed, the mixture cooled, washed with water, dried with magnesium sulfate and solvent removed under reduced pressure to produce the O,S-dimethyl ester (See, FIG. 1.) Examples of synthesized compounds include, O,S-dimethylpropylphosphonothioate, O,S-dimethylbenzylphosphonothioate, 6-(methoxymethylsulfanylphosphoryl)hexanoic acid tert-butyl ester and 7-(methoxymethylsulfanylphosphorylmethyl)naphthalene-1-carboxylic acid tert-butyl ester.

The O,S-dimethyl ester (See, FIG. 1) is then reacted with iodotrimethylsilane to produce the disilyl ester (See, FIG. 1) This is accomplished by dissolving the O,S-dimethyl ester in dichloromethane and cooling the mixture with, for example, with an ice bath before the addition of iodotrimethylsilane. The ice bath is then removed after addition of iodotrimethylsilane and the reaction mixture is left at room temperature for about 6 to 14 hours. The volatiles are then removed under reduced pressure in accordance with standard procedure.

The disilyl ester (See, FIG. 1) is then hydrolyzed to produce the final thiophosphonate product. For example trimethylamine, aniline and p-toluidine are bases useful in this step. Any mildly strong base (inorganic hydroxides, alkyl amines including primary, secondary and tertiary (for example ammonia, trimethylamine) and aromatic amines or heterocyclic amines, for example pyridine or imidazole) can be used. Hydrolysis occurs after reaction with either water or methanol and a base.

Thiophosphonates able of production with this method are, without limitation, the trimethylammonium salt of propylphosphonothioic acid, the trimethylanunonium salt of benzylphosphonothioic acid, the anilinium salt of 6-thiophosphonohexanoic acid methyl ester, the p-methylanilinium salt of 6-thiophosphonohexanoid acid and p-methylanilinium salt of 7-thiophosphonomethylnaphthalene-1-carboxylic acid.

In using the synthetic scheme of the present invention, only the most rudimentary purification of intermediates is necessary. The crude O,O-dimethyl esters are monodeprotect with trimethylamine to produce the intermediate products and two of those products precipitate from solution. The crude salts of O-methylphosphonothioic acid or their aqueous solutions can then be treated with methyl iodide to form the corresponding O,S-dimethyl ester (See, Quin, L. D. (2000) "The acids of organophosphorus chemistry and their derivatives", in: A Guide to Organophosphorus Chemistry, pp. 155–156 John Wiley & Sons, New York.).

These intermediate products of the present invention need not be purified beyond simple washing with water, drying, and removal of volatiles in order to produce a large quantity of high-quality product. The O,S-dimethyl ester is easily di-dealkylated by trimethylsilyl iodide under mild conditions. After removal of volatile materials under reduced pressure the silyl esters are hydrolyzed with either methanol or water in the presence of a base. This crude material, after removal of volatiles, can then be dissolved in acetone and treated with either trimethyl amine or with aniline to give the salts of the final products, which then easily crystallize from the reaction mixture.

Although the demethylation with trimethylamine of the present invention (Spande, T. F. "Synthesis of two novel phosphorylcholine etsters for probes in immunological studies." *J. Org. Chem.* 45, (1980) 3081–3084.) is a slow process, it was found to produce a vastly superior yield than methods utilizing n-butylamine (See, Thuong, N. T. and Chabrier, J. P. "Contribution a l'etude de l'isomerisation des sels acides thiophosphoriques et thiophosphoniques." *Bull. Soc. Chim. France,* (1970) 780–787.), thiourea or sodium iodide (See, Zabirov, N. G., Cherkasov, R. A. and Pudovik, A. N. "Lawesson's reagent in the synthesis of organophosphorus compounds. I. Preparation of diaikyl thiophosphites and alkyl thiophosphonites." *Russ. J. Gen. Chem.* 56, (1986) 1047–1048).

In a comparative analysis, refluxing with n-butylamine in benzene for 24 hours gave 11% of recovered substrate, and, after alkylation with methyl iodide, only 24% of propylphosphonothioic acid O,S-dimethyl ester was obtained. A similar reaction with thiourea in boiling ethanol gave 14% recovered substrate and, after alkylation, gave 22% of recovered substrate. In contrast, the synthetic methods of the present invention have been demonstrated to average a final yield of at least 76% recovered substrate (See Example 1).

Compounds of the Present Invention:

The compounds of the present invention structurally resemble the substrates of the phosphatase enzymes, but bear a nonhydrolyzable thiophosphonate group in place of the phosphate ester moiety present in natural substrates. Such compounds show significant abilities to bind to the active site of such enzymes and thus to inhibit their activity in catalysis. The R group can be hydrogen, any aryl, substituted aryl or alkyl or substituted group without specific limitation. Advantageously, the synthesis method of the instant invention provides for the production of a wide variety of compounds bearing different R groups. In accordance with the invention the identity of the R group determines the specificity of the inhibition for a particular phosphatase. Thus, each compound has a constant thiophosphonyl group and a R group tailored to effectively inhibit a particular phosphatase enzyme.

Examples of the novel compounds of the present invention have formula:

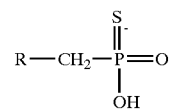

wherein R is selected from an carbonyl substituted alkyl of from about 3 to about 20 carbon atoms; or a mono, di, or tricyclic carbonyl substituted aryl and specifically trimethylammonium salt of propylphosphonothioic acid; the trimethylammonium salt of benzylphosphonothioic acid; the aniliniurn salt of 6-thiophosphonohexanoic acid methyl ester, the pmethylanilinium salt of 6-thiophosphonohexanoid acid; and, p-methylanilinium salt of 7-thiophosphonomethylnaphthalene-1-carboxylic acid.

Effective inhibition of phosphatase enzymes, is accomplished by contacting the phosphatase enzyme to be inhibited with an effective amount of a class of compounds represented by the general formula

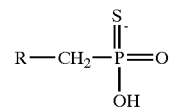

wherein R is hydrogen, an aryl or alkyl group; and, specifically wherein R is selected from the group consisting essentially of hydrogen, methyl, ethyl, phenyl, a carboxyl, or naphthyl or a carbonyl substituted, alkyl of from 3 to 20 carbon atoms, a mono cyclic, bicyclic or polycyclic aryl or substituted aryl, exhibit a high degree of interference with the active region of the phosphatase enzyme and particularly metallophosphatase enzymes and are not hydrolyzed by the enzyme to provide an effective phosphatase enzyme inhibitor. In accordance with the invention, certain of the phosphatase inhibitor compositions are novel. For example those not enabled by the syntheses methods of the prior art. Human alkaline phosphatases are effectively inhibited by use of the above compounds where R is a hydrogen, propyl, benzyl, or methyl group. (See, FIG. 2.) In accordance with another aspect, *E. Coli* alkaline phosphatase is effectively inhibited by use of the above compounds wherein R is a methyl group (See, FIG. 2.) In accordance with another aspect, PP2C are effectively inhibited by use of the above compounds wherein R is a propyl or benzyl group (See, FIG. 2.)

Inhibition of Phosphatase Enzymes:

In general, phosphatases catalyze the transfer of a phosphoryl group from a phosphomonoester or a phosphoanhydride to water, which produces an inorganic phosphate. Classification of phosphatases may be done on the basis of their substrate specificity. This classification system produces nonspecific phosphatases that catalyze hydrolysis of many substrates, phosphoprotein-specific phosphatases that accept phosphorylated proteins or peptides as substrates; and small-molecule specific phosphatases that hydrolyze a specific small molecule phosphate. The phosphoprotein-specific phosphatases can be further divided into those specific for proteins phosphorylated on tyrosine (protein-tyrosine phosphatases, those specific for proteins phosphorylated on serine or on threonine residues [serine-threonine phosphatases); and those specific for any of the three residues listed above.

The catalytic sites of serine/threonine phosphatases and of alkaline phosphatases contain a binuclear metal center and transfer the phosphoryl group directly to a metal-coordinated oxygen nucleophile. Hence, this group is of enzymes are referred to as metallophosphatases. In contrast, the protein-tyrosine phosphatases do not contain metal ions and utilize a cysteine nucleophile to form a phosphorylated cysteine intermediate. The dual-specificity phosphatases, which accept as substrates both serine/threonine phosphates and tyrosine phosphates, do not contain a metal catalytic site and function in a similar manner to the protein-tyrosine phosrhatases.

In accordance with the invention, the inventive compositions have been shown to be effective competitive phosphatase enzyme inhibitors as set forth above. One measure of the level of inhibition of phosphatase enzymes is defined as a low effective concentration as set out below. Basically, the lower the effective concentration of the substance to be an effective inhibitor the better the inhibition power of the substance.

To be an effective phosphatase enzyme competitive inhibitor a substance must compete directly with a normal substrate for an enzymatic-binding site. The most common measure of the affinity of an inhibitor for the active site, and hence of its inhibitory power, is the inhibition constant, or $K_i$. A mathematical equation for the rate of an enzymatic reaction in the presence of an inhibitor is:

$$\frac{1}{v} = \frac{K_m}{V_{\max}}\left(1 + \frac{[I]}{K_i}\right)\frac{1}{[S]} + \frac{1}{V_{\max}}$$

where v=the initial rate at substrate concentration [S]
$K_m$=the Michaelis constant for the substrate
$V_{max}$=the maximum rate at saturating substrate concentration
[I]=inhibitor concentration Initial rates are measured using a fixed substrate concentration, at varying inhibitor concentrations. A second substrate concentration is then used, and a second set of initial rates is measured at varying inhibitor concentrations. This is repeated to produce a set of data that are plotted on a graph of 1/v on the y-axis, and 1/[S] on the x-axis. Competitive inhibition will produce a set of lines that intersect on or very close to the y-axis. The slopes of these lines are then plotted versus the inhibitor concentration [I]; the resulting straight line intersects the x-axis at a point to the left of the origin, equal to $-K_i$.

The lower the value for $K_I$, the greater is the degree of inhibition. The $K_I$, is equivalent to the concentration of inhibitor that doubles the slope of the 1/v versus 1/[S] plot. In particular embodiments, the phosphatase enzymes are selected from the group consisting of the PPM family, the alkaline phosphatase family and the protein-tyrosine family. In a preferred embodiment, the phosphatase enzyme is PP2C. In another preferred embodiment, the phosphatase enzyme is alkaline phosphatase. In a third preferred embodiment, the phosphatase enzyme is human alkaline phosphatase. In another preferred embodiment, the phosphatase enzyme is bacterial, plant, yeast, or mammal PP2C.

Analogues and/or Salts:

In certain embodiments, a pharmaceutically acceptable salt of a compound of the present invention may be created and utilized for any of the methods of the present invention. In addition to the compounds and their pharmaceutically acceptable salts, the invention is further directed, where applicable, to solvated as well as unsolvated forms of the compounds (e.g., hydrated forms) having the ability to regulate and/or modulate phosphatase activity. Any process, known to be applicable to the preparation of chemically related compounds, may be used to prepare the compounds described above. Suitable processes are illustrated by the representative examples provided, infra. Necessary starting materials may be obtained by standard chemical procedures.

Effective Dosage:

Pharmaceutical compositions suitable for use in the present invention include compositions wherein the active ingredients are contained in an effective amount to achieve its intended purpose. More specifically, a therapeutically effective amount means an amount effective to prevent development of or to alleviate the exising symptoms of the subject being treated. Determination of the effective amounts is well within the capability of those skilled in the art, especially in light of the detailed disclosure provided herein.

An effective dose may include a compound of the present invention in an amount capable of decreasing the enzymatic rate, as measured by $K_i$. In a certain embodiment, a compound of the present invention is capable of producing a mM $K_i$. In a particular embodiment, the $K_i$ ranges from 1 mM to 999 mM. In another embodiment, a compound of the present invention is capable of producing a uM $K_i$. In a particular embodiment of the invention, the $K_i$ ranges from 1 uM to 999 uM. In a preferred embodiment, the $K_i$ ranges from 20 uM to 600 uM. In another embodiment, a compound of the present invention is capable of producing a nM $K_i$. In a particular embodiment, the $K_i$ ranges from 1 nM to 999 nM. Such methods of producing an endogenous $K_i$ in any of the above ranges are well known in the art.

In addition, for any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the PTP activity). Such information can be used to more accurately determine useful doses in humans.

Essentially, a therapeutically effective dose refers to that amount of the compound that result in amelioration of symptoms or a prolongation of survival in a patient. Toxicity and therapeutic efficacy of such compounds can be determined by any standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds, which exhibit high therapeutic indices, are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p1).

Dosage amount and interval may be adjusted individually to provide plasma levels of the active moiety, which are sufficient to maintain the phosphatase modulating effects, or minimal effective concentration (MEC). The MEC will vary for each compound but can be estimated from in vitro data; e.g., the concentration necessary to achieve a 50–90% inhibition of the phosphatase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen, which maintains plasma levels above the MEC for 10–90% of the time, preferably between 30–90% and most preferably between 50–90%.

Usual patient dosages for systemic administration range from 1 to 2000 mg/day, commonly from 1 to 250 mg/day, and typically from 10 to 10 to 150 mg/day. Stand in terms of patient body weight, usual dosages range from 0.02 to 25 mg/kg/day, commonly from 0.02 to 3 mg/kg/day, typically from 0.2 to 1.5 mg/kg/day. Stated in terms of patient body surface areas, usual dosages range from 0.5 to 1200 mg/m.sup.2/day, commonly from 0.5 to 150 mg/m.sup.2/day, typically from 5 to 100 mg/m.sup.2/day. Usual average plasma levels should be maintained within 50 to 5000 ug/ml, commonly 50 to 1000 ug/ml, occasionally 100 to 500 ug/ml and sometimes 50 to 5000 pg/ml. (In cases of local administration or selective uptake, the effective local concentration of the drug may not be related to plasma concentration. The amount of composition administered will, of course, be dependent on the subject being treated, on the subject's weight, the severity of the affliction, the manner of administration and the judgment of the prescribing physician.

Desirable blood levels may be maintained by a continuous infusion of the compound as ascertained by plasma levels measured by HPLC. It should be noted that the attending physician would know how to and when to terminate, interrupt or adjust therapy to lower dosage due to toxicity, or bone marrow, liver or kidney dysfunctions. Conversely, the attending physician would also know to adjust treatment to higher levels if the clinical response is not adequate (precluding toxicity).

The magnitude of a preventive or therapeutic dose of the compound in the acute or chronic management of disease will vary with the severity of the condition to be treated and the route of administration. Again, it should be noted that the clinician or physician skilled in the art would know when to interrupt and/or adjust the treatment dose due to toxicity or bone marrow, liver or kidney dysfunctions. The dose, and perhaps the dosage frequency, will also vary according to the age, body weight, and response of the individual patient. In general, as discussed above, the total daily dose ranges for the compounds for the majority of the disorders described herein, is from about 0.02 to about 25 mg/kg patient. Preferably, a daily dose range should be between about 0.02 to about 3 mg/kg, while most preferably a daily dose range should be between about 0.2 to about 1.5 mg/kg per day. It is further recommended that infants and patients over 65 years, and those with impaired renal, or hepatic function, initially receive low doses, and that they be titrated based on individual clinical response(s) and blood level(s). It may be necessary to use dosages outside these ranges in some cases as will be apparent to those of ordinary skill in the art.

Methods of Treatment or Prevention of Disease:

Compounds of the present invention inhibit the activity of phosphatase enzymes, including metallophosphatases, which may be useful in treatment of diseases related to dysfunctional signal transduction, including diabetes and cancer. Alternatively, such composition may act directly on the cells responsible for the disease (e.g., tumor cells) More particularly, the compositions of the present invention may be included in methods for treating, among other diseases, diabetic retinopathy, virual infection, such as HIV, glioma, melanoma, Kaposi's sarcoma, hemangioma and ovarian, breast, lung, pancreatic, prostate, colon and epidermoid cancer.

Any compound of the invention, which inhibits or diminishes the protein-tyrosine-phosphatase (PTP) activity in a signaling pathway may be used in the therapeutic methods of the invention. In a preferred embodiment, the activity of the compound is sufficiently specific for the metallophosphatases in the pathway so that the compound does not interfere with the function of other phosphatases, including protein-tyrosine phosphatases, in the cell. Compounds of the invention are capable of such inhibition of serine/threonine phosphatase and alkaline phosphatase activity (See FIG. 2). Identification and evaluation of such compounds are well known in the art.

The compounds and pharmaceutical compositions of the invention can be used for preventing or treating transplantation rejection. Transplantation rejection is a common occurrence due to biological incompatibility between the donor and recipient that is always present except for transplants between identical twins. This incompatibility causes the recipient to try to destroy or reject the new organ, tissue or cell and will lead to transplantation failure or patient death. Surgical methods of transplantation and transplantation grafts have greatly improved but rejection remains a barrier to saving lives through transplantation. Compounds of the present invention can be used to prevent transplantation rejection through such mechanisms as immunosuppression or induction of donor-specific tolerance.

The compounds and pharmaceutical compositions of the invention may be used to treat immune disorders in which cytokine signal transduction is deficient. Cytokines plays a crucial role in hemopoiesis as well as coordinating immune and inflammatory responses. The compounds may be used to replace or enhance the activity of a cytokine in signaling the differentiation and proliferation of hemopoietic cells, as well as B and T cells in response to antigenic stimulation, and thus be useful for treating anemia and immunodeficiency. The compounds may also be used as an anti-inflammatory agent to treat disorders such as rheumatoid arthritis. The compounds may also be therapeutically useful in treating neurodegenerative diseases, such as multiple sclerosis, by stimulating the growth and differentiation of neuronal cells, which is regulated by neurotrophin-mediated signal transduction.

The compounds and pharmaceutical compositions of the invention can be used for treating diabetes mellitus. The pathogenesis of diabetes generally involves insufficient or a total lack of insulin signal transduction. The paucity or absence of the insulin signal may be caused by a variety of reasons such as a lack of insulin, loss of binding affinity, defective receptor or under expression of receptor. Using the compounds of the invention, insulin receptor activity can be modulated by inhibiting the phosphatases in the signaling. Unlike currently available treatment modalities that are based on the insulin receptor, the insulin signal may be restored or stimulated in cells through the inhibition of dephosphorylating activity, even in the absence of insulin. The example of diabetes mellitus illustrates the principles of therapeutic applications of the invention, which may be applied, to other disorders that implicate signal transduction by phosphotyrosine phosphatases.

In another embodiment of the invention, the compounds and pharmaceutical compositions of the invention may be used to treat cancer, such as leukemia or breast cancer. In a particular embodiment, breast cancer is prevented or treated by administering a compound of the present invention in order to decrease alkaline phosphatase activity. Alkaline phosphatase activity has been shown to be high in human breast cancer cells and compounds of the present invention can inhibit that activity. In alternative embodiments, the compounds and methods of the present invention may be used to treat cancers such as glioma, melanoma, Kaposi's sarcoma, hemangioma and ovarian, lung, pancreatic, liver, prostate, colon and epidermoid cancer, in which the malignant cells proliferate and/or metastasize as a result of uncontrolled signal transduction mediated by growth factors. For example, overexpression of protein tyrosine kinase, such as HER2 has been shown to correlate with the aberrant growth characteristics of tumor cells. The compounds may also inhibit Vasculogenesis and/or angiogenesis that facilitate tumor growth. The compounds may modulate signal transduction in these tumor cells so that normal growth characteristics are restored. The compounds may also be useful in treating psoriasis, which is caused by excessive epidermal growth factor mediated signal transduction.

Pharmaceutical Compositions and Routes of Administration:

The present invention also provides methods of preventing or treating a wide variety of diseases, comprising administering a therapeutic amount of a compound. In particular embodiments, such disease is an autoimmune disease, such as rheumatoid arthritis or multiple sclerosis; rejection of a transplanted organ or tissue; a viral infection, such as HIV; diabetes; a bacterial infection; or cancer, such as breast cancer or leukemia. In an alternative embodiment, a therapeutically effective amount of a compound of Formulas I can be administered with a pharmaceutically acceptable carrier or excipient. In another alternative embodiment, the therapeutically effective amounts of a compound from Formulas I can further include an analogue or salt.

Aqueous compositions of the present invention comprise an effective amount of a therapeutic compound of the present invention, which may be dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

Aqueous compositions of the present invention comprise an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety, and purity standards as required by FDA and other regulatory agency standards. The active compounds will generally be formulated for parenteral administration, e.g., formulated for injection via the intravenous, intramuscular, sub-cutaneous, intralesional, or even intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi.

Solutions of the active compounds can be prepared in water suitably mixed with a surfactant, such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms. The carrier can also be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580).

The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject.

The active therapeutic agents may be formulated within a mixture to comprise about 0.0001 to 1.0 milligrams, or about 0.001 to 0.1 milligrams, or about 1.0 to 100 milligrams or even about 0.01 to 1.0 grams per dose or so. Multiple doses can also be administered.

In addition to the compounds formulated for parenteral administration, such as intravenous or intramuscular injection, other alternative methods of administration of the present invention may also be used, including but not limited to intradermal administration (See U.S. Pat. Nos. 5,997,501; 5,848,991; and 5,527,288), pulmonary administration (See U.S. Pat. Nos. 6,361,760; 6,060,069; and 6,041,775), buccal administration (See U.S. Pat. Nos. 6,375,975; and 6,284,262), transdermal administration (See U.S. Pat. Nos. 6,348,210; and 6,322,808) and transmucosal administration (See U.S. Pat. No. 5,656,284). All such methods of administration are well known in the art.

One may also use intranasal administration of the present invention, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, iactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied, and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor.

In addition, alternative suitable compositions of the present invention may be used, including but not limited to hydrogels (See U.S. Pat. Nos. 6,372,813; 6,372,248; and 6,367,929), vaginal rings (See U.S. Pat. Nos. 6,103,256; and 5,788,980) patches (See U.S. Pat. Nos. 6,238,284; and 5,736,154), crystals (See U.S. Pat. No. 5,827,531), gels (See U.S. Pat. No. 5,830,506), liposomes (See U.S. Pat. Nos. 6,339,069; and 6,143,716) and implants (See U.S. Pat. Nos. 6,251,418; and 5,874,098). All such compositions are well known in the art.

EXAMPLES

General Experimental Protocol:

All reactions in the Examples were performed in oven-flame-dried glassware under nitrogen. Lawesson's reagent was prepared from anisole and phosphorus pentasulfide. (See, Randall, D. I. and Wynn, R. W. (1975) in: Secondary "2-Chloroethylphosphonothioic acids and esters for regulation of plant growth." Patent, GAF Corporation, United States. All organic chemicals were purchased from Acros Organics (Geel, Belgium) unless otherwise stated. All solvents and inorganic chemicals were purchased from Fisher Scientific (Springfield, N.J.). All chemicals and solvents were used without purification. All melting points are uncorrected. All reactions with thiophosphorus compounds were carried out under a nitrogen atmosphere. Atlantic Microlabs performed the elemental analyses (Norcross, Ga.). $^1$H NMR spectra were recorded at 400 MHz in methylsulfoxide-$d_6$ solutions using tetramethylsilane as an internal standard. $^{31}$P NMR spectra were recorded at 162 MHz in methylsulfoxide-$d_6$ solutions using 85% phosphoric acid as an external standard.

It was experimentally determined that freshly prepared Lawesson's Reagent resulted in a higher yield than commercially available reagent (See, Example 1.) Freshly prepared reagent resulted in a 66.9% conversion rate compared to 47.7% for commercially prepared reagent.

1-Iodopropane and benzyl chloride were commercial products. 6-Bromohexanoic acid tert-butyl ester was synthesized by passing isobutylene through solution of 6-bromohexanoic acid in dichlomethane in presence of concentrated sulfuric acid (See, Lecher, H. Z., Greenwood, R. A., Whitehouse, K. C. and Chao, T. H. "The Phosphonation of Aromatic Compounds with Phosphorus Pentasulfide." J. Am. Chem. Soc. 78, (1956) 5018–5022.) and used directly without purification in the next step of the synthetic process. Dimethyl thiophosphite was produced by refluxing dimethyl phosphite (Sigma-Aldrich, St. Louis, Mo.) with Lawesson's reagent in benzene. (Snatzke, G. and Kunde, K. "Perhydrodibenz[a.j]anthracen-14-one, I. Synthese 2-substituierter Dibenz[a.j]anthracen-Derivate." Chem. Ber. 106, (1973) 1341–1362) 7-Methylnaphthalene-1-carboxylic acid was prepared by acetylation of 2-methylnaphthalene to 1-(7-methyl-naphthalen-1-yl)-ethanone followed by oxidation with bromine. (See, Hilgetag, G. and Teichmann, H. "Uber einige Methylierungsreactionen der beiden isomeren Trimethylthiophosphate." J. Prakt. Chem. 8, (1959) 90–96.)

Synthesis of 7-Bromomethylnaphthalene-1-carboxylic acid:

A suspension of N-bromosuccinimide (6.23 g, 0.035 mol) in a solution of 7-methylnaphthalene-1-carboxylic acid (6.2 g, 0.033 mol) in tetrachlomethane (200 mL) was refluxed in the presence trace amounts of benzoyl peroxide for 2 hours. The resulting white suspension was evaporated to dryness under reduced pressure, washed with hot water and dried to give the crude product (8.46 g, 95.8%). An analytical sample was recrystallized from benzene-ethanol mixture. M.p. 209.5–211° C. $^1$H NMR δ 13.20 (bs, 1H), 8.91 (bs, 1H), 8.30–7.95 (m, 3H), 7.72–7.54 (m, 2H), 4.92 (s, 2H). Anal. Calcd for $C_{12}H_9BrO_2$: C, 54.37; H, 3.42. Found: C, 54.45; H, 3.44.

Synthesis of 7-Bromomethylnaphthalene-1-carboxylic acid tert-butyl ester:

Isobutylene was passed through a suspension of 7-bromomethylnaphthalene-1-carboxylic acid (10.4 g, 39.2 mmol) in dichloromethane (150 mL) in the presence of concentrated sulfuric acid (1 mL) for 3 hours, and then the mixture was stirred overnight. The resulting deep green solution was washed with a saturated solution of sodium hydrogen carbonate, dried (magnesium sulfate) and the solvent was removed under reduced pressure to give crude 7-bromomethylnaphthalene-1-carboxylic acid tert-butyl ester (11.2 g, 88.8%) as a deep green oil. This compound was directly used for the subsequent Michaelis-Becker alkylation without further purification.

Synthesis of Propylphosphonothioic acid, trimethylammonium salt:

A solution of dimethyl thiophosphite (10.00 g, 79.4 mmol), 1-iodopropane (11.71 g, 95.2 mmol) and triethylbenzylammonium chloride (1.81 g, 7.94 mmol) in dichlomethane (200 mL) was cooled on an ice bath and a solution of sodium hydroxide (32 g, 0.8 mol) in water (32 mL) was added slowly with vigorous stirring. The ice bath was then removed and the reaction mixture stirred overnight. The next morning, the reaction mixture was washed with water, dried (magnesium sulfate) and solvent removed under reduced pressure to afford crude O,O-dimethylpropylphosphonothioate (9.4 g). This material was then dissolved in acetone (50 mL), liquid trimethylamine (20 mL) was added, and the mixture left at room temperature for 7 days. Precipitated white crystals were filtered off, washed with acetone, and dried over phosphorus pentaoxide to give extremely hygroscopic crude tetramethylammonium O-methylpropylphosphonothioate (7.40 g). This material was dissolved in dichloromethane (250 mL) before iodomethane (9 mL) was added (a precipitate formed immediately) and the suspension was refluxed for 3 hours. The mixture was cooled, washed with water, dried (magnesium sulfate), and solvent was removed under reduced pressure to give crude O,S-dimethylpropylphosphonothioate (4.48 g). This material was dissolved in dichloromethane (20 mL), cooled on an ice bath, and iodotrimethylsilane (12.36 g) was added. After 1 hour the ice bath was removed and the solution left overnight. Volatiles were then removed under reduced pressure, and the residual red oil was dissolved in methanol (50 mL). Solvent was then removed under reduced pressure, the residual red oil dissolved in acetone (20 mL) and subsequently saturated with gaseous trimethylamine (the solution became colorless). After removal of solvent under reduced pressure the colorless oil slowly crystallized to give the trimethylammonium salt of propylphosphonothioic acid (1a) (5.54 g, 35.0% total yield from dimethyl thiophosphite). An analytical sample was recrystallized from acetone-diethyl ether mixture. M.p. 96–100° C. $^1$H NMR δ 2.64 (s, 9H), 1.62–1.48 (m, 4H), 0.92 (t, J=7.1 Hz, 3H). $^{31}$P NMR δ 75.0. Anal. Calcd for $C_6H_{18}NO_2PS$: C, 36.17; H, 9.11; N, 7.03. Found: C, 36.10; H, 9.01; N, 6.94.

Synthesis of Benzylphosphonothioic acid, trimethylammonium salt:

A mixture of dimethyl thiophosphite) (10.02 g, 79.5 mmol), benzyl chloride (See FIG. 1) (11.07 g, 87.5 mmol), dibenzo-18-crown-6 (1.43 g, 4 mmol) and anhydrous potassium carbonate (16.49 g, 0.119 mol) in acetonitrile (240 mL) was vigorously stirred for 3 days. Insoluble material was filtered off, acetonitrile removed by rotary evaporation, and the residue dissolved in dichloromethane (100 mL). This solution was washed with water, dried (magnesium sulfate), and the solvent was removed under reduced pressure. The residual material was then dissolved in warm acetone (100 mL), cooled, and a precipitate of crown ether (1.08 g) was filtered off. Removal of acetone from the filtrate yielded crude O,O-dimethylbenzylphosphonothioate (14.24 g) contaminated mainly with remaining crown ether and dibenzyl sulfide (according to GCMS). The crude O,O-dimethylbenzylphosphonothioate was dissolved in acetone (50 mL), liquid trimethylamine (30 mL) was added, and the mixture left in room temperature for 7 days. Precipitated white crystals were filtered off, washed with acetone, and dried over phosphorus pentaoxide to give crude tetramethylammonium O-methylbenzylphosphonothioate (12.30 g). This material was dissolved in dichlomethane (300 mL) before adding iodomethane (14 mL) (a precipitate formed, immediately) and the resulting suspension was refluxed for 3 hours. After cooling, the mixture was washed with water, dried (magnesium sulfate), and the solvent removed under reduced pressure to give crude O,S-dimethylbenzylphosphonothioate (8.37 g) as white crystals.

A portion of this material (3.67 g) was dissolved in dichlomethane (20 mL), cooled with an ice bath, and iodotrimethylsilane (7.87 g) was added. After 1 hour the ice bath was removed and the solution left overnight. The next morning volatiles were removed under reduced pressure, and the residual red oil was dissolved in methanol (50 mL). Solvent was then removed under reduced pressure, the residual red oil dissolved in acetone (20 mL) and then saturated with gaseous trimethylamine (the solution became colorless). After removal of solvent under reduced pressure the colorless oil slowly crystallized to give the trimethylammonium salt of benzylphosphonothioic acid (3.49 g, 40.5% total yield from dimethyl thiophosphite). An analytical sample was recrystallized from acetone. M.p. 152–154° C.

(with decomposition). $^1$H NMR δ 7.32–7.09 (m, 5H), 3.03 (d, J=18.3 Hz), 2.48 (s, 9H). $^{31}$P NMR δ 68.1. Anal. Calcd for $C_{10}H_{18}NO_2PS$: C, 48.57; H, 7.34; N, 5.66. Found: C, 48.66; H, 7.36; N, 5.69.

Synthesis of 6-Thiophosphonohexanoic acid methyl ester, anilinium salt:

A solution of dimethylthiophosphite (4.56 g, 36.2 mmol), 6-bromohexanoic acid tert-butyl ester (100 g, 39.8 mmol) and triethylbenzylammonium chloride (0.82 g, 3.62 mmol) in dichloromethane (100 mL) was cooled on an ice bath and a solution of sodium hydroxide (14.5 g, 0.362 mol) in water (14.5 mL) was added slowly with vigorous stirring. The ice bath was removed and the mixture stirred for 3 days before being washed with water, dried (magnesium sulfate), and the solvent removed under reduced pressure to give crude 6-(dimethoxythiophosphoryl)hexanoic acid tert-butyl ester (8.00 g).

This material was dissolved in acetone (30 mL), liquid trimethylamine (20 mL) was added, and the mixture was then left at room temperature for 2 weeks. After two weeks, the solvent was removed by rotary evaporation and the residue was dissolved in water (30 mL) before extraction with dichloromethane. The aqueous solution of tetramethylammonium salt of 6-(hydroxymethoxythiophosphoryl) hexanoic acid tert-butyl ester was concentrated to a small volume and mixed with dichlomethane (100 mL). Iodomethane (10 mL) was then added (a precipitate formed immediately) and the suspension was refluxed for 3 hours. After cooling the mixture was washed with water, dried (magnesium sulfate), and the solvent was removed under reduced pressure to give crude 6-(methoxymethylsulfanylphosphoryl)hexanoic acid tert-butyl ester (4.06 g).

This material was dissolved in dichlomethane (20 mL), cooled on ice bath, and iodotrimethylsilane (8.96 g) was added. After 1 hour the bath was removed and the solution left overnight. The next morning volatiles were removed under vacuum, and the residual red oil boiled with methanol (50 mL). Solvent was then removed under reduced pressure, the red residual oil dissolved in methanol (10 mL) and aniline (4 g) was added to the methanol solution (the solution became colorless). After removing the solvent under vacuum, diethyl ether (20 mL) was added and the resulting white precipitate was collected by filtration, washed with ether, and dried to give the anilinium salt of 6-thiophosphonohexanoic aced methyl ester (See FIG. 1) (2.87 g, 24.8% total yield from dimethyl thiophosphite). An analytical sample was recrystallized from acetone-diethyl ether mixture. M.p. 107–108° C. $^1$H NMR δ 7.03–6.97 (m, 2H), 6.58–6.45 (m, 3H), 3.58 (s, 3H), 2.28 (t, 7.4 Hz), 1.80–1.68 (m, 2H), 1.60–1.46 (m, 2H), 1.60–1.46 (m, 4H), 1.40–1.26 (m, 2H). $^{31}$P NMR δ 87.0. Anal. Calcd for $C_{13}H_{22}NO_4PS$: C, 48.89; H, 6.94; N, 4.39. Found: C, 49.02; H, 6.91; N, 4.31.

Synthesis of 6-Thiophosphonohexanoic acid, p-methylanilinium salt:

Using the same procedure as described above from dimethyl thiophosphite (See FIG. 1) (9.12 g, 72.4 mmol), an aqueous solution (100 mL) of crude 6-(hydroxymethoxythiophosphoryl)hexanoic acid tert-butyl ester (See FIG. 1) was obtained. To this solution ethanol (200 mL) and iodomethane (20 mL) were added, and the mixture was refluxed for 3 hours. Solvents were then removed by rotary evaporation, and the residue was dissolved in ethyl acetate (200 mL). This mixture was extracted with water, dried (magnesium sulfate) and solvents were removed under reduced pressure to give crude 6-(methoxymethylsulfanylphosphoryl)hexanoic acid tert-butyl ester (10.33 g).

A portion of this material (3.22 g) was reacted with iodotrimethylsilane as described for 6-thiophosphonohexanoic acid methyl ester and then treated with cold water (10 mL) instead of methanol. Volatiles were removed under vacuum before the residue was dissolved in diethyl ether (10 mL) and p-toluidine (3.5 g) in ether (10 mL). The resulting white precipitate was collected by filtration, washed repeatedly with ether, and dried to give the p-methylanilinium salt of 6-thiophosphonohexanoic acid (2.42 g, 33.6% total yield from dimethyl thiophosphite). An analytical sample was recrystallized from ethanol-acetone-diethyl ether mixture. M.p. 167–168° C. (with decomposition). $^1$H NMR δ 6.83 (d, J=7.6 Hz, 2H), 6.49 (d, J=8.1, 2H), 2.19 (t, J=7.4 Hz, 2H), 2.12 (s, 3H), 1.80–1.68 (m, 2H), 1.60–1.45 (m, 4H), 1.39–1.29 (m, 2H), $^{31}$P NMR δ 87.0 Anal. Calcd for $C_{13}H_{22}NO_4PS$: C, 48.89; H, 6.94; N, 4.39. Found: C, 48.80; H, 6.98; N, 4.35.

Synthesis of 7-Thiophosphonomethylnaphthalene-1-carboxylic acid, p-methylanilinium salt:

A solution of dimethyl thiophosphite (3.84 g, 30.5 mmol), crude 7-bromomethylnaphthalene-1-carboxylic acid tert-butyl ester (11.2 g, 34.9 mmol) and triethylbenzylammonium chloride (0.72 g, 3.17 mmol) in dichloromethane (100 mL) was cooled on an ice bath and a solution of sodium hydroxide (12.7 g, 0.317 mol) in water (12.7 mL) was added slowly with vigorous stirring. The ice bath was then removed and the mixture stirred overnight. The next morning, it was washed with water, dried (magnesium sulfate), and the solvent removed under reduced pressure to give crude 7-(dimethoxythiophosphorylmethyl) naphthalene-1-carboxylic acid tert-butyl ester (See FIG. 1) (10.38 g) as orange oil.

This material was dissolved in acetone (30 mL) before liquid trimethylamine (25 mL) was added. This mixture left at room temperature for 2 weeks. Two weeks later, solvent was removed by rotary evaporation and the residue was dissolved in water (50 mL). This solution was then extracted with ethyl acetate. Ethanol (150 mL) and iodomethane (10 mL) were then added to the aqueous layer and the mixture refluxed for 3 hours. Solvents were removed by rotary evaporation, the residue dissolved in ethyl acetate (125 mL) and then extracted with water. The organic layer was dried (magnesium sulfate) and the solvent removed under reduced pressure to give crude 7-(methoxymethylsulfanylphosphorylmethyl) naphthalene-1-carboxylic acid tert-butyl ester (4.44 g) as thick orange oil.

This material was reacted with iodotrimethylsilane (8.00 g) in dichloromethane (25 mL) as above. Then a water-dioxane mixture (1:1, 20 mL) was added, after which volatiles were removed under vacuum. The residue was then dissolved in a diethyl ether-acetone mixture (4:1, 50 mL) and p-toluidine (3.9 g) in ether (20 mL) was added. The resulting white precipitate was collected by filtration, washed with ether, and dried to give the p-methylanilinium salt of 7-thiophosphonomethylnaphthalene-1-carboxylic acid (4.39 g, 37.0% total yield from dimethyl thiophosphite). An analytical sample was recrystallized from an ethanol-acetone-diethyl ether mixture. M.p. 200–201° C. (with decomposition). $^1$H NMR δ 8.75–8.71 (m, 1H), 8.13–8.07 (m, 2H), 7.91 (d, J=8.6 Hz, 1H), 7.58–7.49 (m, 2H), 6.85 (d, J=7.6 Hz, 2H), 6.54 (d, J=8.1 Hz, 2H), 3.42 (d, J=18.8 Hz, 2H), 2.13 (s, 3H). $^{31}$P NMR δ 79.7. Anal. Calcd for $C_{19}H_{20}NO_4PS$: C, 58.60; H, 5.18; N, 3.60. Found: C, 58.48; H, 5.21; N, 3.41.

What is claimed is:

1. A method for the preparation of the mono-protonated thiophosphonate salts of the general formula

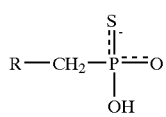

wherein R is selected from the group consisting essentially of hydrogen, methyl, ethyl, phenyl, a carboxyl, or naphthyl substituted or a carbonyl substituted, alkyl of from 3 to 20 carbon atoms, a mono cyclic, bicyclic or polycyclic aryl or substituted aryl comprising the steps of:
   (a) heating a mixture of dimethyl phosphite and Lawesson's reagent in the presence of suitable organic solvent to produce a thiophosphite ester;
   (b) performing an Michaelis-Becker alkylation reaction by contacting a halide of the general formula R—CH$_2$—X, wherein X is a halide, in the presence of a base and a phase transfer catalyst with said thiophosphite ester to produce the corresponding R substituted O,O-dimethyl ester;
   (c) producing the corresponding O-methylphosphonothioic acid, tetramethylammonium salt by addition of an excess of trimethylamine;
   (d) heating the O-methylphosphonothioic acid, tetramethylammonium salt in the presence of a solvent with a stoicheiometric amount of methyl iodide to yield the corresponding O-S-dimethyl ester;
   (e) contacting the cooled O—S-dimethyl ester with iodotrimethylsilane to produce the corresponding disilyl ester;
   (f) hydrolyzing the corresponding disilyl ester; and,
   (g) precipitating the corresponding thiophosphonate salt from the corresponding disilyl ester in the presence of a base.

2. The method of claim 1 further comprising removing said suitable organic solvent under reduced pressure and vacuum distillation of the residue prior to performing said Michaelis-Becker alkylation reaction.

3. The method of claim 1 wherein said corresponding R substituted O,O-dimethyl ester is extracted from the Michaelis-Becker alkylation reaction mixture by first washing the reaction mixture with water followed by drying the residual non-aqueous layer and evaporating the remaining solvent.

4. The method of claim 1 wherein said excess of trimethylamine is added in the presence of a solvent, and filtering the precipitated product.

5. The method of claim 1 further comprising: washing the post reaction mixture from step (d) with water followed by drying the residual non-aqueous layer and evaporating the remaining solvent.

6. The method of claim 1 wherein said R is selected from the group consisting of imidazole, indole, pyrrole, morpholine, isoxazole, pyrazole, amino acid, or a polypeptide.

7. The method of claim 1 wherein X is bromine.

8. The method of claim 1, wherein R is selected from the group consisting of propyl, benzyl, 6-hexanyl-carboxylic acid, 7-1 methanylnaphthalene-carboxylic acid, 6-hexanyl carboxylic acid methyl ester.

9. The method of claim 1, wherein the base added to the thiophosphite ester is selected from the group consisting of sodium hydroxide, and anhydrous potassium carbonate or DBU, or an amine.

* * * * *

UNITED STATES PATENT AND TRADEMARK OFFICE
CERTIFICATE OF CORRECTION

| | | |
|---|---|---|
| PATENT NO. | : 6,943,267 B1 | Page 1 of 1 |
| APPLICATION NO. | : 10/346672 | |
| DATED | : September 13, 2005 | |
| INVENTOR(S) | : Alvan Carl Hengge and Krzysztof Jerzy Swierczek | |

It is certified that error appears in the above-identified patent and that said Letters Patent is hereby corrected as shown below:

Col. 1, lines 12-13 should read,

Federal Support Clause

This invention was made with Government support under GM047297 awarded by the National Institutes of Health. The Government has certain rights in this invention.

Signed and Sealed this
Fifth Day of April, 2011

David J. Kappos
*Director of the United States Patent and Trademark Office*